United States Patent
Moszner et al.

(10) Patent No.: US 7,365,222 B2
(45) Date of Patent: *Apr. 29, 2008

(54) POLYMERIZABLE BICYCLIC CYCLOPROPANE DERIVATIVES AND THEIR USE FOR THE PREPARATION OF DENTAL MATERIALS

(75) Inventors: Norbert Moszner, Eschen (LI); Armin de Meijere, Göttingen (DE); Frank Zeuner, Vaduz (LI); Urs Karl Fischer, Arbon (CH)

(73) Assignee: Ivoclar Vivadent AG, Schaan (LI)

( * ) Notice: Subject to any disclaimer, the term of this patent is extended or adjusted under 35 U.S.C. 154(b) by 386 days.

This patent is subject to a terminal disclaimer.

(21) Appl. No.: 10/658,993

(22) Filed: Sep. 10, 2003

(65) Prior Publication Data

US 2004/0077882 A1 Apr. 22, 2004

(30) Foreign Application Priority Data

Oct. 22, 2002 (DE) ............................... 102 49 324

(51) Int. Cl.
C07C 69/74 (2006.01)
C07D 265/00 (2006.01)
C07D 311/02 (2006.01)
A01N 37/00 (2006.01)

(52) U.S. Cl. ..................... 560/124; 504/313; 549/283

(58) Field of Classification Search ................ 560/124; 504/313

See application file for complete search history.

(56) References Cited

U.S. PATENT DOCUMENTS

| 4,567,030 | A | 1/1986 | Yuasa et al. |
| 6,136,887 | A | 10/2000 | Moszner et al. |
| 6,900,251 | B2 | 5/2005 | Moszner et al. |
| 6,953,832 | B2 | 10/2005 | Moszner et al. |
| 2006/0178469 | A1* | 8/2006 | Moszner et al. ............. 524/556 |

FOREIGN PATENT DOCUMENTS

| DE | 196 12 004 C2 | 10/1997 |
| DE | 198 12 888 C2 | 1/1999 |
| EP | 1 025 830 | 8/2000 |

OTHER PUBLICATIONS

Capps et al., Synthesis of Bicyclic Pyridone and Dihydropyridone Analogues of β-Lactam Antibiotics, *J. Chem. Soc. Perkin Trans.*, 1:3077-3086 (1991).
Moszner et al., "Synthesis and Polymerization of Vinylcyclopropanes," *Macromol. Chem. Phys.*, 200:2173-2187 (1999).
Sanda et al., "Radical Copolymerization of 1,1-Bis(ethoxycarbonyl)-2-vinylcyclopropane and Methyl Methacrylate Accompanying Ring Opening and Cyclization," *Macromoecules*, 27:3982-3985 (1994).
Warmerdam et al., "Synthesis of (R)- and (S)-2-hydroxy-3-enoic Acid Esters," *Recl. Trav. Chim. Pays-Bas*, 115:20-24 (1996).
Yang et al., "Exploring New Reactive Species for Cyclopropanation," *Tetrahedron Letters*, 39:8621-8624 (1998).
Mueller et al., "Ring Expansion Synthesis of Fused trans-α-Methylene γ-Lactones," *Journal of Organic Chemistry* 44:4741-4742 (1979).
Moszner et al., "Polymerization of Cyclic Monomers, 10$^{a,b}$: Synthesis and Radical Polymerization of Methyl 2-(Bicyclo[3.1.0]hex-1-yl)acrylate," *Macromolecular Rapid Communications* 24:269-273 (2003).
Sanda et al., "Synthesis and Radical Polymerization of Spiroorthocarbonates Bearing Exo-Methylene Groups," *Macromolecules*, American Chemical Society 4:737-743 (1993).
Sanda et al., "Radical Polymerization of 3,9-Dimethylene-1,5,7,11-tetraoxaspiro[5.5]undecane. Study of the Structure of the Polymer and Mechanism of Polymerization," *Macromolecules*, American Chemical Society 4:729-736 (1993).
Moszner et al., "Polymerization of Cyclic Monomers," *Polymer Bulletin* 40:477-453 (1998).
Sanda et al., "Radical Ring-Opening Polymerization of Novel Vinylcyclopropanes Designed as Low Shrinking Monomers. Structure of the Polymer, Mechanism of the Polymerization, and Volume Change of the Polymerization," *Macromolecules*, American Chemical Society 28:1346-1355 (1995).
Dietliker, "Photoinitiators for Pigmented Media," in Fouassier et al., eds., Radiation Curing in Polymer Science and Technology—Photoinitiating Systems, vol. II, London and New York: Elsevier Applied Science, pp. 155-237 (1993).
"Radical Polymerization," Encyclopedia of Polymer Science and Engineering, vol. 13, New York, New York: John Wiley & Sons, pp. 754 ff. (1088).

(Continued)

Primary Examiner—Tae H Yoon
(74) Attorney, Agent, or Firm—Nixon Peabody LLP

(57) ABSTRACT

Bicyclic cyclopropane derivatives of the general Formula (I)

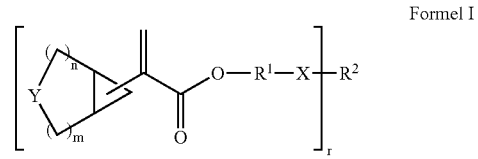

Formel I in which n+m is 0 to 8; r is 1 to 4; $R^1$ is absent or is a $C_1$-$C_{20}$ alkylene radical which can be interrupted by O or S, a cycloaliphatic $C_4$-$C_{12}$ radical, a bicyclic $C_4$-$C_{12}$ radical, a $C_6$-$C_{14}$ arylene or $C_7$-$C_{20}$ alkylenearylene radical; $R^2$ is for r=1 a $C_1$-$C_{20}$ alkyl radical which can be interrupted by O or S, a cycloaliphatic $C_4$-$C_{12}$ radical, a bicyclic $C_4$-$C_{12}$ radical, a $C_6$-$C_{14}$ aryl or a $C_7$-$C_{20}$ alkylaryl radical; is for r>1 an r-times substituted aliphatic $C_1$ to $C_{20}$ radical which can be interrupted by O or S, a cycloaliphatic $C_4$-$C_{12}$ radical, an aromatic $C_6$-$C_{14}$ radical or aliphatic-aromatic $C_7$-$C_{20}$ radical; X is absent or is —CO—O—, —CO—NH— or —O—CO—NH—, and Y is $CH_2$, O or S which is suitable in particular for the preparation of dental materials.

7 Claims, No Drawings

OTHER PUBLICATIONS

Okazaki et al., "Synthesis and Radical Ring-Opening Polymerization Behavior of Bifunctional Vinylcyclopropane Bearing a Spiroacetal Moiety," Macromolecules 28:6026-6028 (1995).

Sanda et al., "Synthesis and Radical Ring-Opening Polymerization of a Vinylcyclopropane Bearing a Cyclic Carbonat Moiety, 1-Vinyl-5,7-dioxaspior[2.5]octan-6-one," Macromolecules 27:3986-3991 (1994).

Tietze et al., "Reaktionen und Synthesen im Organisch-Chemischen Praktikum und Forschungs-Laboratorium," Stuttgart and New York: Georg Thieme Verlag, pp. 62, 266 (1991).

* cited by examiner

POLYMERIZABLE BICYCLIC CYCLOPROPANE DERIVATIVES AND THEIR USE FOR THE PREPARATION OF DENTAL MATERIALS

The present invention relates to polymerizable bicyclic cyclopropane derivatives, which are suitable in particular for the preparation of dental materials.

1,1-Disubstituted 2-vinylcyclopropanes have become increasingly interesting as radically polymerizable monomers, as in the case of ring-opening polymerization compared with polymerization of linear vinyl monomers, such as e.g. methacrylates, a lower volume contraction takes place (N. Moszner, F. Zeuner, T. Volkel, V. Rheinberger, Macromol. Chem. Phys. 200 (1999) 2173). Sanda et al. have examined the copolymerization of 1,1-bis(ethoxycarbonyl)-2-vinylcyclopropane (ECVCP) with methyl methacrylate (MMA) (F. Sanda, T. Takata, T. Endo, Macromolecules, 27 (1994) 3982). The results found show that ECVCP is characterized by a lower radical polymerization ability compared with MMA, which clearly limits its practical application. The polymerization of ECVCP and methacrylates leads to heterogeously composed products with a low incorporation of the vinylcyclopropane into the copolymer structure, which results in unsatisfactory mechanical properties.

Vinylcyclopropane derivatives and in particular vinylcyclopropane (meth)acrylates are known from DE 198 12 888 A1, which can be well copolymerized with acrylates and methacrylates.

Moreover, vinylcyclopropanes with several groups capable of polymerization are known. F. Sanda, T. Takata, T. Endo, Macromolecules 27 (1994) 3986, describe 1-vinyl-5,7-dioxaspiro[2.5]octan-6-one, a hybrid monomer which contains a vinylcyclopropane and a cyclic carbonate group, and T. Okazaki, F. Sanda, T. Endo, Macromolecules 28 (1995) 6026, 1,10-bis(vinyl)-4,8,12,15-tetraoxatrispiro [2.2.2.2.2.2]pentadecane, a monomer in which two vinylcyclopropane groups are connected to each other via a spiroacetal unit. These compounds are hydrolysis-sensitive and have no improved radical copolymerization capability with (meth)acrylic compounds compared with monofunctional vinylcyclopropanes.

DE 196 12 004 A1 discloses multifunctional vinylcyclopropane derivatives with two to six vinylcyclopropane groups, which allow the preparation of cross-linked polymers.

The object of the invention is to prepare monomers which display a low shrinkage upon radical polymerization and at the same time have a radical polymerization capability comparable to methacrylates.

This object is achieved by bicyclic cyclopropane derivatives of the general Formula (I)

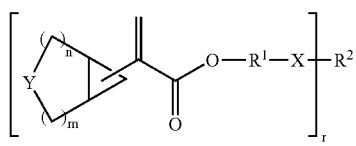

Formel I in which $R^1$, $R^2$, X, Y, n, m and r, independently of one another, have the following meaning:

n+m=0 to 8;
r=1 to 4;

$R^1$=is absent, or a $C_1$-$C_{20}$ alkylene radical which can be interrupted by O or S, a cycloaliphatic $C_4$-$C_{12}$ radical, a bicyclic $C_4$-$C_{12}$ radical, a $C_6$-$C_{14}$ arylene or $C_7$-$C_{20}$ alkylenearylene radical;

$R^2$ is for r=1: a $C_1$-$C_{20}$ alkyl radical which can be interrupted by O or S, a cycloaliphatic $C_4$-$C_{12}$ radical, a bicyclic $C_4$-$C_{12}$ radical, a $C_6$-$C_{14}$ aryl or $C_7$-$C_{20}$ alkylaryl radical;

for r>1: an r-times substituted aliphatic $C_1$ to $C_{20}$ radical which can be interrupted by O or S, a cycloaliphatic $C_4$-$C_{12}$ radical, an aromatic $C_6$-$C_{14}$ radical or aliphatic-aromatic $C_7$-$C_{20}$ radical;

X=is absent, —CO—O—, —CO—NH— or —O—CO—NH— and

Y=$CH_2$, O or S.

The following preferred definitions, which can be selected independently of each other, exist for the variables of Formula (I):

n+m=1 to 5, in particular 2 or 3;
r=1 to 3, in particular 1 or 2;

$R^1$=is absent, or a $C_1$-$C_{10}$ alkylene radical which can be interrupted by O, cyclohexylene, a bicyclic $C_6$-$C_9$ radical, phenylene or a $C_7$-$C_{10}$ alkylenearylene radical, in particular is absent, a —$(CH_2)_{1-4}$ radical which can be interrupted by O, cyclohexylene or phenylene;

$R^2$ is for r=1: a $C_1$-$C_6$ alkyl radical which can be interrupted by O, a cycloaliphatic or bicyclic $C_6$-$C_8$ radical, a $C_6$-$C_{10}$ aryl or $C_7$-$C_{10}$ alkylaryl radical, in particular a $C_1$-$C_4$ alkyl radical which can be interrupted by O, cyclohexyl, bicyclo[2.2.1]heptyl;

for r>1: an r-times substituted aliphatic $C_1$ to $C_{12}$ radical which can be interrupted by O, a cycloaliphatic $C_5$-$C_7$ radical, an aromatic $C_6$-$C_{10}$ radical or aliphatic-aromatic $C_7$-$C_{10}$ radical, in particular an r-times substituted aliphatic $C_2$ to $C_6$ radical, an r-valent cyclohexane radical or an r-valent benzene radical;

X=is absent, —CO—O— or —O—CO—NH—, in particular is absent or —CO—O— and

Y=$CH_2$ or O, in particular $CH_2$.

Naturally such bicyclic cyclopropane derivatives are particularly preferred in which all variables have one of the preferred or particularly preferred meanings.

The fact that a radical can be interrupted by foreign atoms such as oxygen or sulphur, is to be understood to mean that one or more of the foreign atoms are integrated into a carbon chain. It follows from this that the foreign atoms cannot be terminal, i.e. a connection to neighbouring groups always takes place via a carbon atom, and that the number of foreign atoms must inevitably be smaller than the number of carbon atoms. Groups which have a maximum of 4, preferably a maximum of 2 foreign atoms are preferred. The aforementioned also applies by analogy to branched groups.

All place-isomeric and stereoisomeric forms and mixtures of different place-isomeric and stereoisomeric forms, such as e.g. racemates, are covered by Formula (I). As Formula (I) reveals, the radical —C(=$CH_2$)—C(=O)—O—$R^1$—X—$R^2$ can be bonded to the cyclopropane ring via a bridgehead atom or the bridge atom.

The radicals $R^1$ and $R^2$ can be substituted one or more times and can be unsubstituted. Preferred substituents for $R^1$ are alkyl, halogen, $OCH_3$, $OC_2H_5$, vinyl, propenyl, (meth)acryl, $COOR^3$ and mesogenic groups.

Preferred substituents for $R^2$ are for r=1 alkyl, halogen, $OCH_3$, $OC_2H_5$, vinyl, propenyl, (meth)acryl, $COOR^3$, $SiCl_3$, $Si(OR^4)_3$, or mesogenic groups. Preferred substituents for r>1 are alkyl, halogen, $OCH_3$, $OC_2H_5$, vinyl, propenyl, (meth)acryl, CO—$OR^3$ and mesogenic groups.

Unless otherwise stated, alkyl preferably stands for $C_1$ to $C_{10}$ alkyl, in particular $C_1$ to $C_4$ alkyl. Preferred halogen substituents are F, Cl, Br and I.

In all cases $R^3$ has the meaning H, $C_1$ to $C_{10}$ alkyl, in particular $C_1$ to $C_4$ alkyl, or phenyl, and $R^4$ the meaning H or $C_1$ to $C_{10}$ alkyl, in particular $C_1$ to $C_4$ alkyl.

By mesogenic groups are meant radicals which can form so-called mesophases, i.e. liquid-crystal phases. Preferred mesogenic groups are:

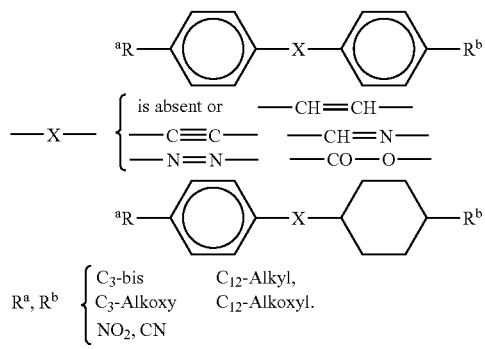

Bicyclic cyclopropane derivatives in which the radicals are unsubstituted or substituted once are preferred.

The bicyclic cyclopropane derivatives according to the invention of the general Formula (I) ($R^1$, X is absent, r=1) can be obtained starting from cycloalkenecarbaldehydes:

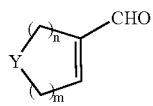

These can be prepared from cycloalkenes via 1,2-dihydroxycycloalkanes by stepwise oxidation (L. F. Tietze, T. Eicher, *Reaktionen and Synthesen* Thieme Verlag Stuttgart, 1991 p. 62 and 266). By the addition of hydrocyanic acid to the cycloalkenecarbaldehyde and subsequent alcoholysis 2-(cycloalkene-1-yl)-2-hydroxyacetic ester is obtained (E. G. J. C. Warmerdam, A. M. C. H. van den Nieuwendijk, C. G. Kruse, J. Brussee, A. van der Gen, Rec. Trav. Chim. Pays-Bas 115 (1996) 20):

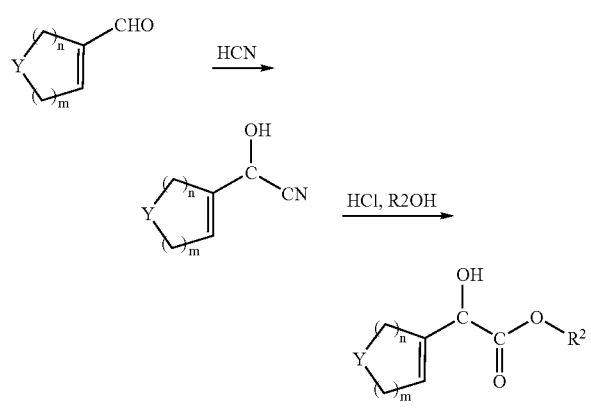

In the next step, the Simmons-Smith cyclopropanation takes place (Zh. Yang, J. C. Lorenz, Y. Shi, Tetrahedron Lett: 39 (1998) 8621):

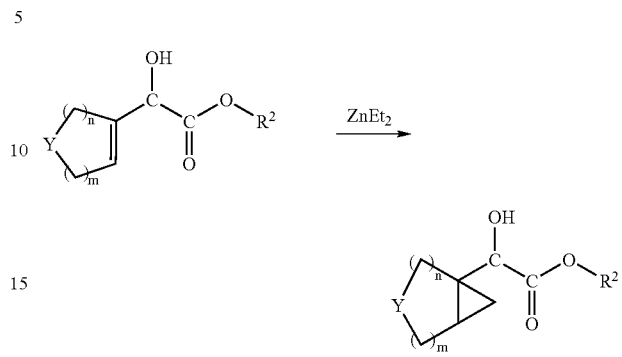

The bicyclo-2-hydroxyacetic esters can then be converted e.g. by oxidation with $MnO_2$ into bicyclo-2-oxo-acetic esters (N. G. Capps, G. M. Davies, D. Loakes, R. W. McCabe, D. W. Young, J. Chem. Soc. Perkin Trans. 1 (1991) 3077). By using a Wittig reaction the bicyclic cyclopropane derivatives of the general Formula (I) are then obtained:

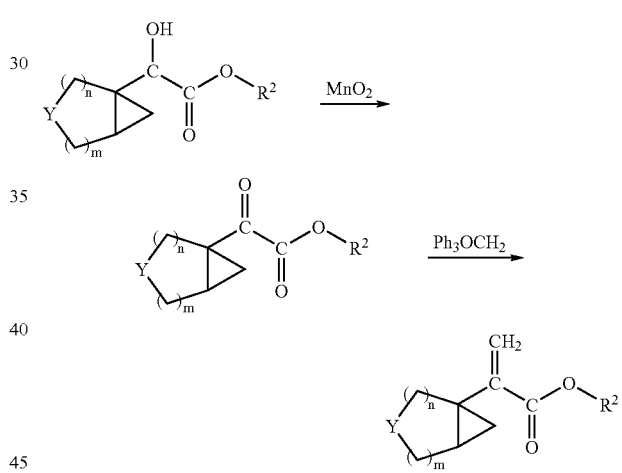

CONCRETE EXAMPLE

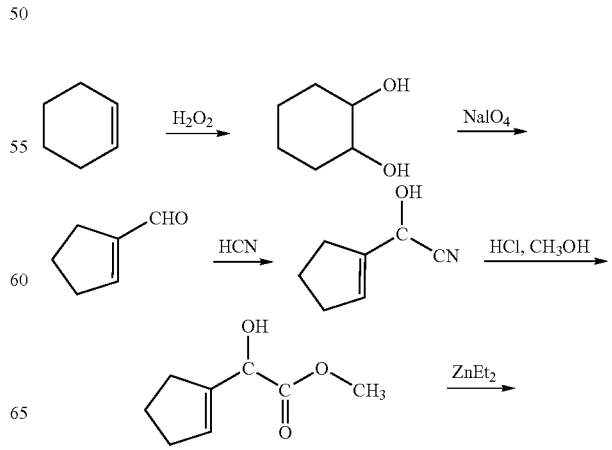

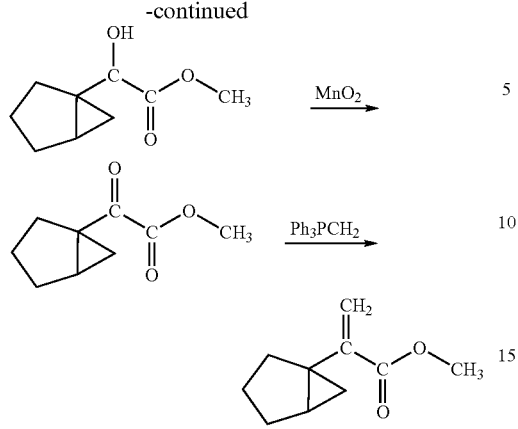

Bicyclic cyclopropane derivatives of the general Formula (I) (r>1, $R^2$ is absent) can be obtained by hydrolysis of bicyclic cyclopropane derivatives (r=1 and $R^1$, X=is absent) and subsequent esterification with polyfunctional alcohols [(HO—$R^1$—X—)$_r$]:

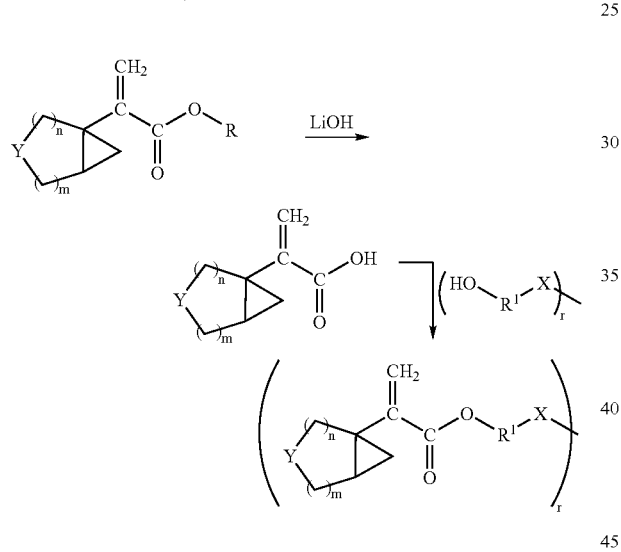

CONCRETE EXAMPLE

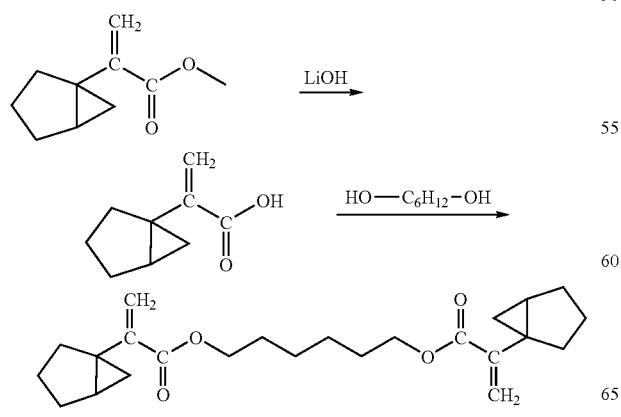

Particularly preferred examples for the bicyclic cyclopropane derivatives of Formula (I) according to the invention are:

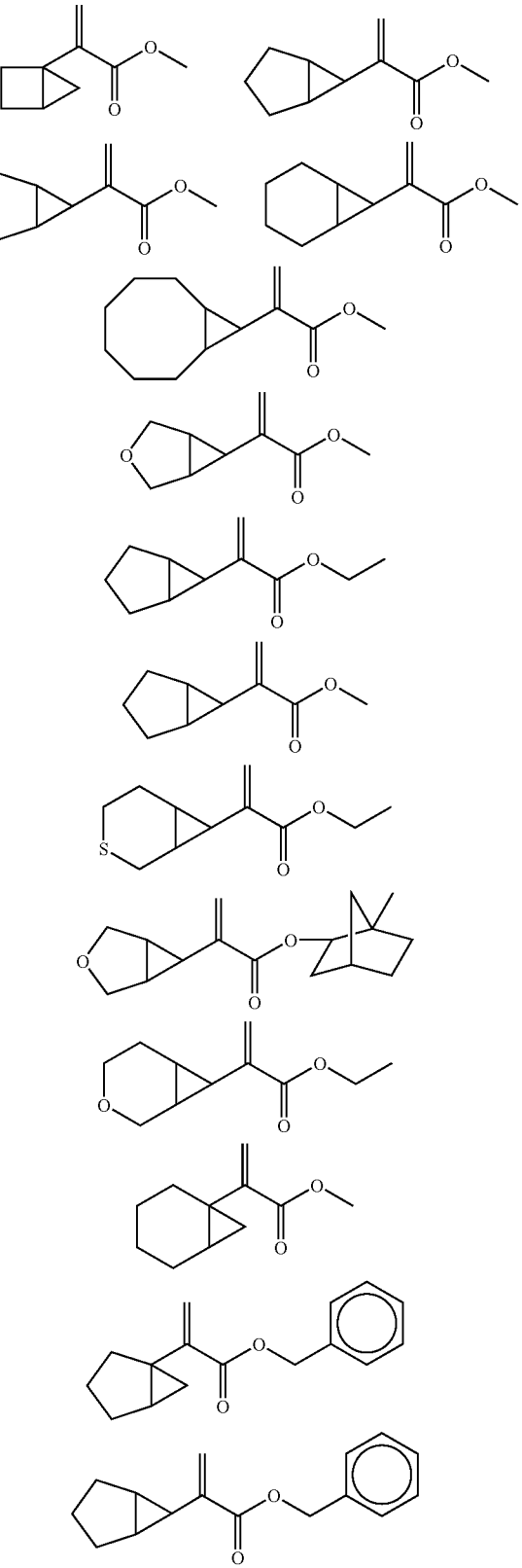

-continued
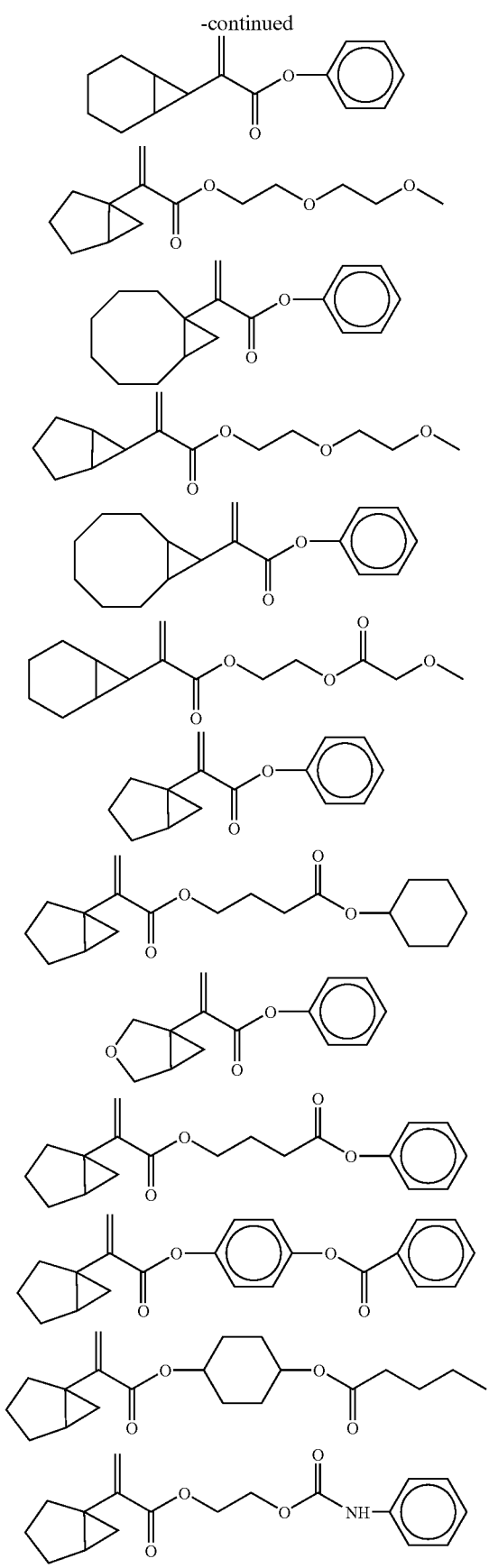
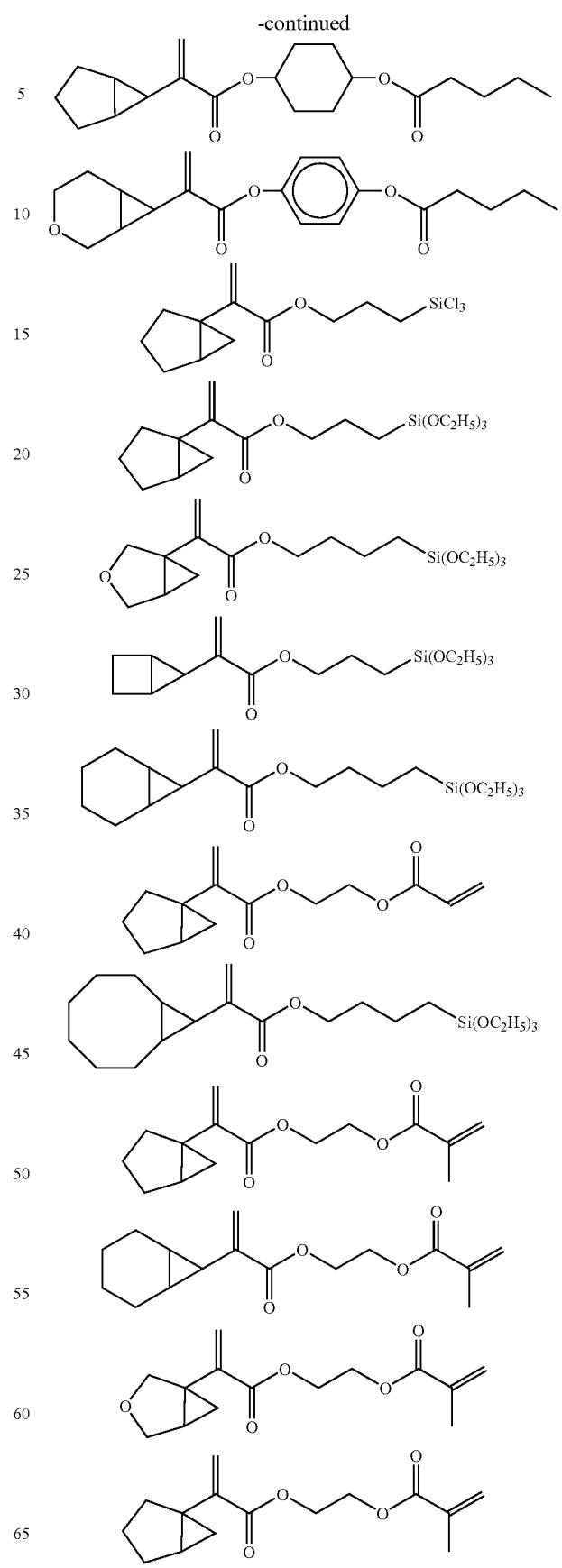

-continued

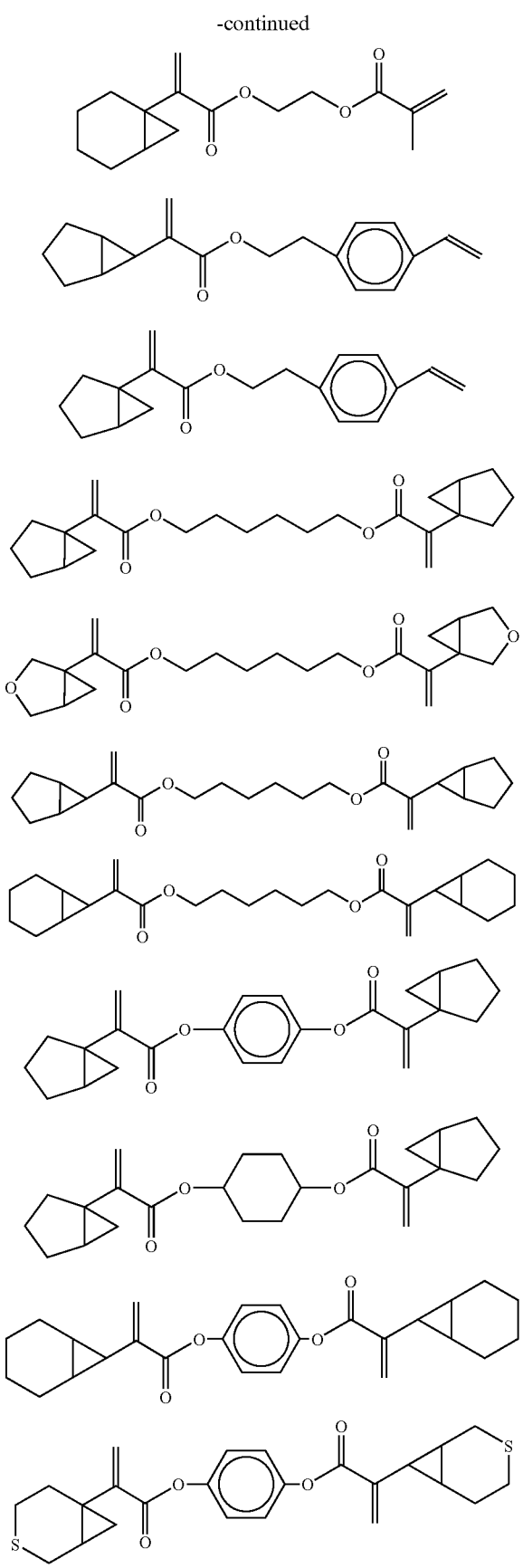
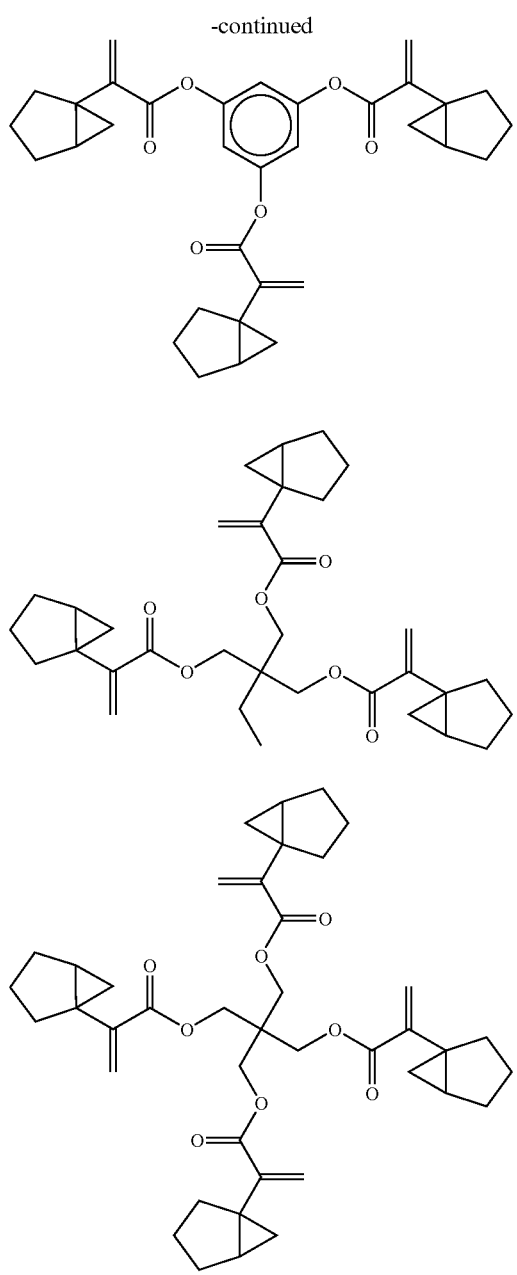

The bicyclic cyclopropane derivatives according to the invention are suitable in particular of or the preparation of polymers and copolymers, shaped bodies, adhesives, coating materials, cements and composites and in particular dental materials.

To this end, they are mixed with an initiator for radical polymerization and preferably also with additional monomers, fillers and optionally further auxiliaries. The thus-obtained compositions can be cured by radical polymerization. Both the cured products, such as e.g. polymers and shaped bodies, and the curable compositions are likewise a subject of the invention.

The known initiators for cold, heat and photocuring are suitable as initiators for radical polymerization. Suitable initiators are described for example in the Encyclopedia of Polymer Science and Engineering, Vol. 13, Wiley-Intersci. Pub., New York etc. 1988, p. 754 ff.

Preferred initiators are azo compounds such as azobis (isobutyronitrile) (AIBN) or azobis(4-cyanovaleric acid) or peroxides such as dibenzoyl peroxide, dilauroyl peroxide, tert.-butyl peroctoate, tert.-butyl perbenzoate or di-(tert.-butyl)-peroxide.

Benzopinacol and 2,2'-di ($C_1$-$C_8$-alkyl)benzopinacols are particularly suitable as initiators for heatcuring.

Suitable photoinitiators for the UV or visible range are described by J. P. Fouassier, J. F. Rabek (Ed.), Radiation Curing in Polymer Science and Technology, Vol. II, Elsevier Applied Science, London and New York 1993, pages 155 to 237. Preferred photoinitiators are benzoin ethers, dialkyl benzil ketals, dialkoxy acetophenones, acylphosphine oxides, bisacylphosphine oxides, α-diketones such as 10-phenanthrenequinone, diacetyl, furil, anisil, 4,4'-dichlorobenzil and 4,4'-dialkoxy benzil and camphorquinone.

Dibenzoyl peroxide, camphorquinone and acylphosphine oxides are preferred for the preparation of dental materials.

To accelerate the initiation by peroxides or α-diketones combinations with aromatic amines are particularly suitable. In addition, redox systems can be used as accelerators, in particular combinations of benzoyl peroxide, lauroyl peroxide or camphorquinone with amines, such as N,N-dimethyl-p-toluidine, N,N-dihydroxyethyl-p-toluidine, p-dimethylaminobenzoic acid ethyl ester or structure-related amines. Moreover redox systems are also suitable which, in addition to peroxide, contain ascorbic acid, a barbiturate or a sulfinic acid as reducing agent.

The bicyclic cyclopropane derivatives according to the invention can be polymerized alone or in admixture with conventional radically polymerizable monomers. Compositions which, in addition to one or more bicyclic cyclopropane derivatives and optionally initiator, also contain one or more radically polymerizable monomers are preferred.

Monofunctional and/or multifunctional radically polymerizable monomers, in particular di-, tri- and tetrafunctional, more particularly preferably difunctional crosslinking monomers are suitable as comonomers. By monofunctional monomers are meant compounds with one, by multifunctional monomers compounds with two and more radically polymerizable groups. Crosslinkable bi- or multifunctional acrylates or methacrylates, such as e.g. Bisphenol-A-di(meth)acrylate, bis-GMA (the addition product of methacrylic acid and Bisphenol-A-diglycidyl ether), UDMA (the addition product of hydroxyethyl methacrylate and 2,2,4-trimethylhexamethylene diisocyanate), di-, tri- or tetraethylene glycol di(meth)acrylate, decanediol di(meth) acrylate, trimethylolpropane tri(meth)acrylate and pentaerythritol tetra(meth)acrylate are above all suitable for the preparation of adhesives, coating materials and dental materials. Butanediol di(meth)acrylate, 1,10-decanediol di(meth) acrylate and 1,12-dodecanediol di(meth)acrylate, which are obtainable by esterification of (meth)acrylic acid with the corresponding diols, are also suitable, as well as di- and multifunctional 2-vinylcyclopropane derivatives which are obtainable by reaction of 1-methoxycarbonyl-2-vinylcyclopropane-1-carboxylic acid with di or trivalent OH or $NH_2$ compounds as coupling components, i.e. e.g. with ethylene glycol, di- or triethylene glycol, butylene glycol, 1,6-hexanediol, glycerol, triethanolamine, trimethylolpropane triol, pentaerythrite or glucose, as well as hydroquinone, resorcin, catechol or pyrogallol, ethylene diamine, propylene diamine, hexamethylene diamine, o-, p- or m-phenylene diamine.

Further multifunctional radically polymerizable monomers, which are particularly suitable as crosslinking monomers, are urethanes from 2-(hydroxymethyl)acrylic acid ethyl ester and diisocyanates such as e.g. 2,2,4-trimethylhexamethylene diisocyanate or isophorone diisocyanate, crosslinking pyrrolidones such as e.g. 1,6-bis(3-vinyl-2-pyrrolidonyl)-hexane, or commercially obtainable bisacrylamides such as methylene or ethylene bisacrylamide, or bis(meth)acrylamides, such as e.g. N,N'-diethyl-1,3-bis (acrylamido)-propane, 1,3-bis (methacrylamido)-propane, 1,4-bis(acrylamido)-butane or N,N'-bis(acryloyl)-piperazine, which can be synthesized by reaction from the corresponding diamines with (meth)acrylic acid chloride. These compounds are characterized by a relatively high hydrolysis stability.

In addition, the acrylamides and hydroxyalkyl acrylamides disclosed in DE 101 01 523 and DE 102 28 540 are suitable as radically polymerizable comonomers.

Preferred monofunctional radically polymerizable monomers which are particularly suitable as diluting monomers, are hydrolysis-stable mono(meth)acrylates such as e.g. mesityl methacrylate, or 2-(alkoxymethyl)acrylic acids such as e.g. 2-(ethoxymethyl) acrylic acid, 2-(hydroxymethyl) acrylic acid, N-mono- or -disubstituted acrylamides such as e.g. N-ethylacrylamide, N,N-dimethacrylamide, N-(2-hydroxyethyl) acrylamide or N-(2-hydroxyethyl)-N-methylacrylamide, as well as N-monosubstituited methacrylamides, such as e.g. N-ethylmethacrylamide or N-(2-hydroxyethyl) methacrylamide and in addition N-vinylpyrrolidone or allyl ether.

All organic and inorganic particles or fibres are suitable as fillers for improving mechanical properties or for adjusting viscosity.

Preferred fillers for the preparation of dental materials such as fixing cements or filling composites are amorphous, spherical materials based on oxides, such as $ZrO_2$ and $TiO_2$, or mixed oxides of $SiO_2$, $ZrO_2$ and/or $TiO_2$ with a mean average particle size of 0.005 to 2.0 μm, preferably from 0.1 to 1 μm, as they are disclosed for example in DE-PS 32 47 800, nanoparticulate or microfine fillers such as pyrogenic silicic acid or precipitated silicic acid, as well as mini fillers, such as quartz, glass ceramic or glass powder, as well as x-ray opaque fillers such as ytterbium fluoride or nanoparticulate tantalum(V)oxide or barium sulphate. By mini fillers are meant fillers with an average particle size from 0.5 to 1.5 μm, preferably 0.01 to 1 μm. In addition glass fibres, polyamide or carbon fibres can also be used.

Moreover, the compositions according to the invention can if necessary contain further auxiliaries, in particular stabilizers, UV-absorbers, dyes, pigments and/or lubricants. By stabilizers are meant such substances which prevent a premature polymerization and thus above all increase the storage stability of monomer mixtures and composites, without however adversely affecting the properties of the cured materials. Preferred stabilizers are hydroquinone monomethyl ether (MEHQ) and 2,6-di-tert.-butyl-4-methylphenol (BHT).

The compositions according to the invention are particularly suitable as dental materials, in particular as dental adhesives, fixing cements or filling composites as well as materials for inlays/onlays, teeth or facing materials for crowns and bridges. They are characterized by a low polymerization shrinkage and, after curing, by very good mechanical properties.

Preferred for use as dental materials are curable compositions which contain a) 1 to 95 wt.-% bicyclic cyclopropane derivative;
b) 0.01 to 5 wt.-% initiator for radical polymerization; and
c) 0 to 94 wt.-% further radically polymerizable monomer.

Particularly suitable for use as adhesive and in particular dental adhesive are compositions which contain
- a) 1 to 80 wt.-%, and particularly preferably 10 to 60 wt.-% bicyclic cyclopropane derivatives according to the invention,
- b) 0.01 to 5 wt.-%, particularly preferably 0.1 to 2.0 wt.-% initiator for radical polymerization,
- c) 0 to 60 wt.-% and particularly preferably 0 to 40 wt.-% further radically polymerizable monomer,
- d) 0 to 20 wt.-% filler and
- e) 0 to 40 wt.-% and particularly preferably 0 to 30 wt.-% solvent.

Particularly suitable for use as cement and in particular dental cement are compositions, which contain
- a) 1 to 60 wt.-%, and particularly preferably 20 to 50 wt.-% bicyclic cyclopropane derivative according to the invention,
- b) 0.01 to 5 wt.-%, particularly preferably 0.1 to 2.0 wt.-% initiator for radical polymerization,
- c) 0 to 60 wt.-% and particularly preferably 0 to 20 wt.-% further radically polymerizable monomer,
- d) 20 to 60 wt.-% and particularly preferably 30 to 60 wt.-% filler.

Particularly suitable for use as filler composite and in particular dental filling composite are compositions which contain
- a) 1 to 45 wt.-%, and particularly preferably 10 to 30 wt.-% bicyclic cyclopropane derivative according to the invention,
- b) 0.01 to 5 wt.-%, particularly preferably 0.1 to 2.0 wt.-% initiator for radical polymerization,
- c) 0 to 50 wt.-% and particularly preferably 0 to 10 wt.-% further radically polymerizable monomer,
- d) 30 to 85 wt.-% and particularly preferably 40 to 80 wt.-% filler.

Particularly suitable for use as coating material and in particular dental coating material are compositions which contain
- a) 1 to 95 wt.-%, and particularly preferably 10 to 60 wt.-% bicyclic cyclopropane derivative according to the invention,
- b) 0.01 to 5 wt.-%, particularly preferably 0.1 to 2.0 wt.-% initiator for radical polymerization,
- c) 0 to 60 wt.-% and particularly preferably 0 to 40 wt.-% further radically polymerizable monomer,
- d) 0 to 20 wt.-% filler.

The invention is explained in more detail in the following examples.

EXAMPLES

Example 1

Stage 1: 2-(bicyclo[3.1.0]hex-1-yl)-2-hydroxyacetic Acid Methyl Ester 23.8 ml (310 mmol) trifluoroacetic acid, dissolved in 25 ml methylene chloride, were added dropwise at −15° C. within 30 minutes to a well-stirred solution of 31.8 ml diethyl zinc (310 mmol) in 400 ml anhydrous methylene chloride, so that the temperature did not exceed 0° C. After a further 15 minutes' stirring at 0° C. 25.1 ml (310 mmol) diiodemethane were added so that the temperature did not exceed 0° C. The mixture was stirred until it was completely homogeneous and then reacted at 0° C. with 22.0 g (141 mmol) 2-(cyclopentene-1-yl)-2-oxyacetic acid methyl ester. The mixture was stirred for a further 12 hours at room temperature, then cooled down to 0° C. and carefully reacted with 310 ml 1M sulphuric acid accompanied by vigorous stirring. The aqueous phase was saturated with sodium chloride and then extracted with diethyl ether. The combined organic phases were washed with 2N caustic soda solution and saturated sodium chloride solution and dried over magnesium sulphate. The solution was concentrated and the residue distilled in vacuum. 22.8 g (95% yield) of a colourless liquid with a boiling point of $Kp_{0.1 Torr}$=53-54° C. was obtained.

IR (film): ν=3490, 3067, 3000, 2953, 2862, 1735 (C=O), 1438, 1273, 1226, 1201, 1085, 1026, 990, 946, 798, 776, 730.

$^1$H-NMR (250 MHz, $CDCl_3$): δ =0.43-0.55 (m, 2H), 1.08-1.30 (m, 1H), 1.36-1.81 (m, 6H), 2.87 (br. s, 1H), 3.79 (s, 3H), 3.99 (s, 1H).

$^{13}$C-NMR (62.9 MHz, $CDCl_3$, DEPT): δ =9.9 (−), 21.1 (−), 22.0 (+), 26.8 (−), 28.3 (−), 31.6 (q), 52.4 (+), 74.3 (+), 175.0 (q).

MS (70 eV, EI), m/z (%): 170.1 (0.8) [M$^+$], 152 (25.4), 137 (5.4), 120 (4.8), 111 (67.5), 93 (25.2), 81 (100.0), 67 (67.5). —$C_9H_{14}O_3$ (170.21): Calc. C 63.51, H 8.29; Found. C 63.28, H 7.99.

Stage 2: 2-(bicyclo[3.1.0]hex-1-yl)-2-oxoacetic Acid Methyl Ester

2×40 g active manganese(IV)oxide were added one after the other over 2 hours to a well-stirred solution of 13.6 g (80 mmol) 2-(bicyclo[3.1.0]hex-1-yl)-2-hydroxyacetic acid methyl ester in 500 ml anhydrous ether, and the mixture was stirred at room temperature for a further 4 hours until all the starting material was used up (DC control). The reaction mixture was then filtered over diatomaceous earth (Celite®). After the solvent was evaporated off in vacuum at room temperature, 10.8 g (80%) of 2-(bicyclo[3.1.0]hex-1-yl)-2-oxoacetic acid methyl ester was obtained as clear light-yellow liquid (purity >96% according to GC), which does not have to be purified further.

IR (film): ν=3008, 2957, 2869, 1734 (C=O), 1684 (C=O), 1453, 1437, 1382, 1293, 1240, 1179, 1081, 1039, 1003, 929, 866, 794.

$^1$H-NMR (250 MHz, $CDCl_3$) δ =1.14, (t, J=5.50 Hz, 1H), 1.18-1.36 (m, 1H), 1.60-1.94 (m, 5H), 2.08-2.22 (m, 1H), 2.31-2.38 (m, 1H), 3.79 (s, 3H).

$^{13}$C-NMR (62.9 MHz, $CDCl_3$, DEPT): δ =19.0 (−), 20.4 (−), 26.5 (_), 26.9 (−), 33.9 (+), 39.3 (q), 52.3 (+), 163.3 (q), 195.8 (q).

MS (70 eV, EI), m/z (%): 168 (0.6) [M$^+$], 140 (1.6), 109 (100.0), 81 (81.3), 79 (41.3).

—$C_9H_{12}O_3$ (168.19): Calc. C 64.27, H 7.19; Found. C 64.55, H 6.96.

Stage 3: 2-(bicyclo[3.1.0]hex-1-yl)acrylic Acid Methyl Ester (BCHAM)

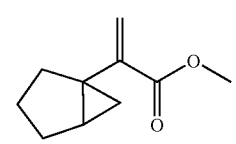

BCHAM 1.4 ml (10 mmol) diisopropylamine and 65 ml (100 mmol) 1.55 M n-BuLi solution in hexane were added under argon at −78° C. to a well-stirred suspension of 37.5 g (105 mmol) methyltriphenylphosphonium bromide in 400 ml anhydrous tetrahydrofuran (THF). The reaction mixture was allowed to heat to room temperature, cooled again and then at −78° C. a solution of 16.8 g (100 mmol) 2-(bicyclo-[3.1.0]hex-1-yl)-2-oxoacetic acid methyl ester in 20 ml THF was added dropwise so that the temperature did not exceed −50° C. The solution was then stirred for 10 hours at room temperature and acidified with 5% sulphuric acid. After the addition of 50 ml saturated sodium chloride solution the organic phase was separated off, the aqueous phase extracted with diethyl ether and the combined organic phase washed with saturated sodium chloride solution. 10 mg 2,6-di-t-butyl-p-cresol (BHT) were added for stabilizing, then the solvent was distilled off and the residue purified by column chromatography (pentane/diethyl ether 20:1). 15.7 g (85% yield) of BCHAM was obtained as colourless liquid.

IR (film): ν=3073, 3001, 2953, 2862, 1725 (C=O), 1624 (C=CH$_2$), 1436, 1366, 1323, 1302, 1216, 1174, 1123, 1018, 996, 941, 856, 812.

$^1$H-NMR (250 MHz, CDCl$_3$) δ =0.63 (d, J=6.00 Hz, 2H), 1.12-1.32 (m, 1H), 1.41-1.47 (m, 1H), 1.57-1.95 (m, 5H), 3.73 (s, 3H), 5.56 (d, J=1.65 Hz, 1H), 6.07 (d, J=1.65 Hz, 1H). $^{13}$C-NMR (62.9 MHz, CDCl$_3$, DEPT): δ =12.9 (−), 21.1 (−), 24.9 (+), 27.5 (−), 30.8 (q), 32.1 (−), 51.5 (+), 124.5 (−), 143.8 (q), 167.4 (q).

MS (70 eV, EI), m/z (%): 166 (37.3) [M$^+$], 151 (15.9), 138 (21.4), 134 (58.7), 106 (95.6), 91 (100.0), 79 (62.2), 77 (39.3), 67 (20.6). —C$_{10}$H$_{14}$O$_2$ (166.09938).

Example 2

Stage 1: 2-(bicyclo[3.1.0]hex-1-yl)acrylic Acid 40 ml (160 mmol) 4N lithium hydroxide was added dropwise in a nitrogen atmosphere to a well-stirred solution of 13.3 g (80 mmol) BCHAM and 10 mg BHT in 160 ml acetone and 20 ml water. The mixture was stirred at room temperature until all the ester was used up (DC control, approx. 24 hours). The solvent was then distilled off, the residue taken up in some water and washed with 2×50 ml diethyl ether followed by acidification with concentrated hydrochloric acid and extraction with ether. The combined ether phases were washed with saturated sodium chloride solution and dried over sodium sulfate. After the solvent was drawn off 10.5 g (86% yield) of a white solid was obtained.

IR (film): ν=3436, 3067, 3028, 3005, 2958, 2937, 2861, 2731, 2601, 1694 (C=O), 1621 (C=CH$_2$), 1426, 1321, 1304, 1253, 1224, 1180, 1134, 1042, 1022, 954, 916, 804.

$^1$H-NMR (250 MHz, CDCl$_3$): δ =0.60-0.70 (m, 2H), 1.13-1.34 (m, 1H), 1.43-1.50 (m, 1H), 1.58-1.97 (m, 5H), 5.71 (d, J=1.62 Hz, 1H), 6.28 (d, J=1.62 Hz, 1H).

$^{13}$C-NMR (62.9 MHz, CDCl$_3$, DEPT): δ =13.0 (_), 21.2 (_), 24.9 (+), 27.5 (_), 30.6 (q), 32.2 (_), 127.3 (_), 143.3 (q), 172.8 (q).

MS (70 eV, EI), m/z (%): 152 (<0.1) [M$^+$], 107 (0.7), 78 (100.0), 77 (18.0), 52 (14.1), 51 (12.7). —C$_9$H$_{12}$O$_2$ (152.19): Calc. C 71.03, H 7.95; Found. C 71.30, H 7.75.

Stage 2: 1,6-bis-[2-bicyclo[3.1.0]hex-1-ylacroyloxy]hexane (BHAH)

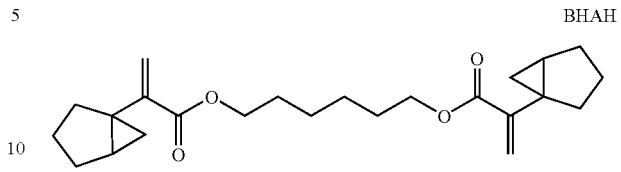

BHAH 12.6 g (72.3 mmol) azodicarboxylic acid diethyl ester were added dropwise to a solution of 11.0 g (72.2 mmol) 2-(bicyclo [3.1.0]hex-1-yl)acrylic acid, 4.27 g (36.1 mmol) 1,6-hexanediol and 19.0 g (72.4 mmol) triphenyl phosphine in 145 ml anhydrous THF accompanied by stirring at −78° C., so that the temperature did not exceed −70° C. The mixture was stirred for 30 minutes, then the cold bath removed and allowed to heat to room temperature. The solvent was removed in vacuum at room temperature and then the residue taken up in 500 ml pentane. The solution was filtered over silica gel, and the silica gel was washed with pentane/diethyl ether (20:1). The solvent was distilled off again in vacuum at room temperature and the remaining residue purified by column chromatography (pentane/diethyl ether, 20:1). 11.7 g (84% yield) of BHAH was obtained as colourless liquid.

IR (film): ν=3067, 3028, 3001, 2953, 2861, 1719 (C=O), 1624 (C=CH$_2$), 1476, 1451, 1364, 1292, 1213, 1175, 1119, 1017, 987, 941, 813.

$^1$H-NMR (250 MHz, CDCl$_3$): δ =0.58-0.66 (m, 4H), 1.12-1.33 (m, 2H), 1.39-1.46 (m, 6H), 1.57-1.74 (m, 8H), 1.77-1.94 (m, 6H), 4.13 (t, J=6.87 Hz, 4H), 5.56 (d, J=1.75 Hz, 2H), 6.09 (d, J=1.75 Hz, 2H).

$^{13}$C-NMR (62.9 MHz, CDCl$_3$, DEPT): δ =12.9 (−), 21.2 (−), 25.1 (+), 25.7 (−), 27.6 (−), 28.5 (−), 30.8 (q), 32.3 (−), 64.3 (+), 124.6 (−), 144.1 (q), 167.1 (q).

MS (70 eV, EI), m/z (%): 386.3 (14.3) [M$^+$], 268 (19.8), 240 (24.6), 152 (38.3), 135 (100.0), 107 (94), 91 (38). —C$_{24}$H$_{34}$O$_4$ (386.24571): 386.2457 (correct HRMS).

Example 3

Radical Homopolymerization of BCHAM in Solution 2.0 mol-% (relative to the monomer) AIBN were added to a solution of BCHAM (2.0 mol/l) in chlorobenzene in a Schlenk vessel. After the monomer solution had been degassed and the Schlenk vessel had been closed under argon, the reaction mixture was polymerized in thermostated water bath at 65° C. After 15 hours, the polymerization was broken off by precipitation of the polymerisate with ten times the amount of methanol. The polymer formed was filtered off and dried to a constant weight. The yield was almost 100% of a white homopolymerisate with a numerically average molar mass of 120,000 g/mol and a glass transition temperature of approx. 90° C. The $^1$H and $^{13}$C-NMR spectra of the polymers formed show that the polymerization of BCHAM has taken place accompanied by the opening of cyclopropane rings.

Example 4

Radical Homopolymerization of BHAH in Bulk

The monomer BHAH was polymerized in bulk with AIBN (2.5 mol-%) at 65° C. A transparent and insoluble polymerisate resulted after 15 hours. The insolubility of the product shows that both polymerizable groups of the starting monomers were extensively incorporated into the polymer network formation.

Example 5

Radical Copolymerization of BCHAM with MMA

Analogous to homopolymerization in solution (Example 3) a monomer mixture of BCHAM (1.0 mol/l), methyl methacrylate (MMA, 1.0 mol/l) and AIBN (2.5 mol-%) were prepared in chlorobenzene and polymerized. The yield of copolymer with a numerically average molar mass of 84,300 g/mol and a glass transition temperature of approx. 85° C. was 45% after 15 minutes. A molar copolymer composition of BCHAM:MMA=1.00:0.63 was determined by means of $^1$H-NMR spectroscopy. This result shows the greater reactivity of bicyclic cyclopropane derivative BCHAM compared with methacrylate MMA.

Example 6

Radical Copolymerization of BCHAM with UDMA

In order to determine the polymerization shrinkage a mixture of 50 vol.-% BCHAM and 50 vol.-% UDMA (the urethane dimethacrylate of 2 mol 2-hydroxyethyl methacrylate and 1 mol 2,2,4-trimethylhexamethylene diisocyanate) was prepared, mixed with 0.3 wt.-%. (relative to the total mixture) camphorquinone (photoinitiator) and 0.4 wt.-% 4-(dimethylamino)-benzoic acid ethyl ester (amine accelerator) and then irradiated with a dental light source (Spectramat, Ivoclar Vivadent AG). A polymerization shrinkage of 7.0% was calculated from the difference between the determined densities of the monomer mixture and the polymerisate formed, taking into account the polymerization shrinkage of pure UDMA ($\Delta_p V$=6.1%). The polymerization shrinkage known for MMA of 20.7% was calculated from the results of the polymerization of an analogous mixture of MMA and UDMA (50:50). Decanediol dimethacrylate has a polymerization shrinkage of 11%.

The comparison of Examples 5 and 6 shows that the bicyclic vinylcyclopropane derivatives according to the invention are characterized, compared to methacrylates, by a higher reactivity and a lower polymerization shrinkage.

Example 7

Preparation of a Dental Cement Based on the Bicyclic Vinylcyclopropane Derivative from Example 1

According to Table 1 given below, a composite fixing cement was prepared on the basis of (A) a methacrylate mixture (comparison example) and (B) the monomer BCHAM from Example 1 by means of a cylinder mill (Exakt type, Exakt Apparatebau, Norderstedt). Test pieces with the measurements 2×2×20 mm were prepared from the materials, which were cured by double irradiation for 3 minutes each with a dental light source (Spectramat, Ivoclar Vivadent AG). Then, the mechanical properties of the test pieces were determined according to the ISO standard 4049.

It can be seen from Table 2 that, after curing, material B according to the invention is comparable in its mechanical properties in every respect to the comparison material A based on a conventional methacrylate mixture.

TABLE 1

Composition of the examined cements

| Component | Material A[1] proportion (wt. -%) | Material B proportion (wt. -%) |
|---|---|---|
| Urethane dimethacrylate[2] | 31.6 | 31.6 |
| Decanediol dimethacrylate | 7.8 | — |
| BCHAM (from Ex. 1) | — | 7.8 |
| Pyrogenic silicic acid (Aerosil OX-50, Degussa) | 41.2 | 41.2 |
| Ytterbium trifluoride (Rhone-Poulenc) | 18.7 | 18.7 |
| Photo initiator[3] | 0.7 | 0.7 |

[1]Comparison example
[2]Urethane dimethacrylate from 2 mol 2-hydroxyethyl methacrylate and 1 mol 2,2,4-trimethylhexamethylene diisocyanate-1,6
[3]1:1 mixture of camphorquinone and N,N-diethyl-3,5-di-tert-butylaniline

TABLE 2

Mechanical properties of the examined cements

| Material properties | Material A[1] | Material B |
|---|---|---|
| Bending strength (MPa) after 24 h | 95 | 104 |
| Bending strength (MPa) after 24 h WS[2] | 101 | 106 |
| Bending strength (MPa) after 7 d WS | 111 | 119 |
| Bending E-modulus (Gpa) after 24 h | 4.71 | 4.78 |
| Bending E-modulus (Gpa) after 24 h WS | 4.90 | 4.69 |
| Bending E-modulus (Gpa) after 7 d WS | 5.13 | 5.14 |

[1]Comparison example
[2]WS = water storage of test pieces

The example shows that dental materials based on bicyclic cyclopropane derivatives according to the invention such as BCHAM, despite improved reactivity and reduced polymerization shrinkage, have no disadvantages regarding the mechanical properties.

The invention claimed is:

1. A bicyclic cyclopropane derivative of the Formula (I)

$$\left[ \begin{array}{c} \underset{Y}{\overset{(\,)_n}{\diagdown}} \hspace{-0.5em} \diagup \hspace{-0.5em} \underset{(\,)_m}{\overset{}{\diagdown}} \overset{\|}{\underset{O}{\diagup}} O - R^1 - X \right]_r R^2$$

in which $R^1$, $R^2$, X, Y, n, m and r, independently of one another, having the following meanings:
n+m=0 to 8;
r=2 to 4;
$R^1$=is absent, or a $C_1$-$C_{20}$ alkylene radical which can be interrupted by O or S, a cycloaliphatic $C_4$-$C_{12}$ radical, a bicyclic $C_4$-$C_{12}$ radical, a $C_6$-$C_{14}$ arylene or $C_7$-$C_{20}$ alkylenearylene radical;

$R^2$=is an r-times substituted aliphatic $C_1$ to $C_{20}$ radical which can be interrupted by O or S, a cycloaliphatic $C_4$-$C_{12}$ radical, an aromatic $C_6$-$C_{14}$ radical or aliphatic-aromatic $C_7$-$C_{20}$ radical;

X=is absent, —CO—O—, —CO—NH— or —O—CO—NH— and

Y=$CH_2$, O or S, wherein $R^2$ is unsubstituted or substituted by alkyl, halogen, $OCH_3$, $OC_2H_5$, vinyl, propenyl, (meth)acryl, CO—$OR^3$ or a mesogenic group, with $R^3$=H or $C_1$ to $C_{10}$ alkyl or a phenyl radical.

2. A bicyclic cyclopropane derivative according to claim 1, wherein at least one variable of the Formula (I) has one of the following meanings:

n+m=1 to 5;

r=2 or 3;

$R^1$=is absent, or a $C_1$-$C_{10}$ alkylene radical which can be interrupted by O, cyclohexylene, a bicyclic $C_6$-$C_9$ radical, phenylene or a $C_7$-$C_{10}$ alkylenearylene radical;

$R^2$=is an r-times substituted aliphatic $C_1$ to $C_{12}$ radical which can be interrupted by O, a cycloaliphatic $C_5$-$C_7$ radical, an aromatic $C_6$-$C_{10}$ radical or aliphatic-aromatic $C_7$-$C_{10}$ radical;

X=is absent, —CO—O— or —O—CO—NH— and

Y=$CH_2$ or O.

3. A bicyclic cyclopropane derivative according to claim 1, wherein at least one variable of the Formula (I) has one of the following meanings:

n+m=2 or 3;

r=2;

$R^1$=is absent, a -$(CH_2)_{1-4}$- radical which can be interrupted by O, cyclohexylene or phenylene;

$R^2$ is an r-times substituted aliphatic $C_2$ to $C_6$ radical, an r-valent cyclohexane radical or an r-valent benzene radical;

X=is absent or —CO—O— and

Y=$CH_2$.

4. A bicyclic cyclopropane derivative of the Formula (I)

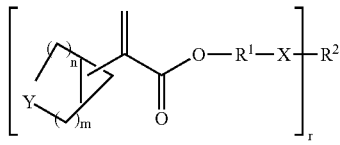

in which $R^1$, $R^2$, X, Y, n, m and r, independently of one another, having the following meanings:

n+m=0 to 8;

r=1 to 4;

$R^1$=is absent, or a $C_1$-$C_{20}$ alkylene radical which can be interrupted by O or a cycloaliphatic $C_4$-$C_{12}$ radical, a bicyclic $C_4$-$C_{12}$ radical, a $C_6$-$C_{14}$ arylene or $C_7$-$C_{20}$ alkylenearylene radical;

$R^2$ is for r=1: a $C_2$-$C_{20}$ alkyl radical which can be interrupted by O or S, a cycloaliphatic $C_4$-$C_{12}$ radical, a bicyclic $C_4$-$C_{12}$ radical, a $C_6$-$C_{14}$ aryl or $C_7$-$C_{20}$ alkylaryl radical;

for r>1: an r-times substituted aliphatic $C_1$ to $C_{20}$ radical which can be interrupted by O or S, a cycloaliphatic $C_4$-$C_{12}$ radical, an aromatic $C_6$-$C_{14}$ radical or aliphatic-aromatic $C_7$-$C_{20}$ radical;

X=is absent, —CO—O—, —CO—NH— or —O—CO—NH— and

Y=$CH_2$, O or S.

5. A bicyclic cyclopropane derivative according to claim 4, wherein at least one variable of the Formula (I) has one of the following meanings:

n+m=1 to 5;

r=1 to 3;

$R^1$=is absent, or a $C_1$-$C_{10}$ alkylene radical which can be interrupted by O, cyclohexylene, a bicyclic $C_6$-$C_9$ radical, phenylene or a $C_7$-$C_{10}$ alkylenearylene radical;

$R^2$ is for r=1: a $C_2$-$C_6$ alkyl radical which can be interrupted by O, a cycloaliphatic or bicyclic $C_6$-$C_8$ radical, a $C_6$-$C_{10}$ aryl or $C_7$-$C_{10}$ alkylaryl radical;

for r>1: an r-times substituted aliphatic $C_1$ to $C_{12}$ radical which can be interrupted by O, a cycloaliphatic $C_5$-$C_7$ radical, an aromatic $C_6$-$C_{10}$ radical or aliphatic-aromatic $C_7$-$C_{10}$ radical;

X=is absent, —CO—O— or —O—CO—NH— and

Y=$CH_2$ or O.

6. A bicyclic cyclopropane derivative according to claim 4, wherein at least one variable of the Formula (I) has one of the following meanings:

n+m=2 or 3;

r=1 or 2;

$R^1$ =is absent, a -$(CH_2)_{1-4}$- radical which can be interrupted by O, cyclohexylene or phenylene;

$R^2$ is for r=1: a $C_2$-$C_4$ alkyl radical which can be interrupted by a O, cyclohexyl, bicyclo[2.2.1]heptyl or;

for r>1: an r-times substituted aliphatic $C_2$ to $C_6$ radical, an r-valent cyclohexane radical or an r-valent benzene radical;

X=is absent or —CO—O— and

Y=$CH_2$.

7. A bicyclic cyclopropane derivative according to claim 4, wherein r is equal to 1 and $R^2$ is unsubstituted or substituted by alkyl, halogen, $OCH_3$, $OC_2H_5$, vinyl, propenyl, (meth)acryl, $COOR^3$, $SiCl_3$, $Si(OR^4)_3$, or a mesogenic group, with $R^3$=H, a $C_1$ to $C_{10}$ alkyl or a phenyl radical and $R^4$=H or a $C_1$ to $C_{10}$ alkyl radical.

* * * * *